United States Patent
Wang et al.

(10) Patent No.: US 8,344,080 B2
(45) Date of Patent: Jan. 1, 2013

(54) CATALYST FOR OLEFIN POLYMERIZATION AND METHOD OF PREPARATION THEREOF

(76) Inventors: Licai Wang, Yingkou (CN); Zhanxian Gao, Dalian (CN); Wei Li, Yingkou (CN); Guotong Zheng, Yingkou (CN); Qingxin Dong, Yingkou (CN); Riping Liu, Dalian (CN); Xiaohuan Wang, Dalian (CN); Nan Zhang, Dalian (CN); Jingzhuang Wang, Yingkou (CN); Shimian Cai, Yingkou (CN)

( * ) Notice: Subject to any disclaimer, the term of this patent is extended or adjusted under 35 U.S.C. 154(b) by 10 days.

(21) Appl. No.: 13/153,997

(22) Filed: Jun. 6, 2011

(65) Prior Publication Data

US 2011/0301385 A1    Dec. 8, 2011

Related U.S. Application Data

(63) Continuation-in-part of application No. 11/659,621, filed on Feb. 6, 2007, now Pat. No. 7,964,678.

(30) Foreign Application Priority Data

Mar. 7, 2005    (CN) .......................... 2005 1 0045990

(51) Int. Cl.
*C08F 4/42*    (2006.01)
(52) U.S. Cl. .................................................. 526/124.3
(58) Field of Classification Search ................ 526/124.3
See application file for complete search history.

(56) References Cited

U.S. PATENT DOCUMENTS

2004/0229748 A1*   11/2004   Chen et al. .................... 502/118

OTHER PUBLICATIONS

Hewgill et al., J.Chem. Soc. C, 1967 p. 2316-2321.*

* cited by examiner

*Primary Examiner* — Rebecca Anderson
*Assistant Examiner* — Sonya Wright
(74) *Attorney, Agent, or Firm* — Squire Sanders (US) LLP

(57) ABSTRACT

A catalyst for olefin polymerization and method of preparing the same are disclosed.

5 Claims, No Drawings

CATALYST FOR OLEFIN POLYMERIZATION AND METHOD OF PREPARATION THEREOF

CROSS-REFERENCE TO RELATED APPLICATIONS

This is a continuation-in-part of U.S. application Ser. No. 11/659,621, filed on Feb. 6, 2007 now U.S. Pat. No. 7,964,678, the teaching of which is incorporated herein in its entirety by reference.

TECHNICAL FIELD

This invention deals with catalysts for olefin polymerization reaction. These catalysts are applicable to the homopolymerization and copolymerization reactions of alfa-olefin such as ethylene, propylene, 1-butene and isobutene.

BACKGROUND ART

Since being invented, Ziegler-Natta catalyst system is developed continuously, which has become the essential aspect of catalyst for industrial olefin polymerization reactions. Currently, almost all industrial polyolefin catalysts are Ziegler-Natta support catalysts, whose development mainly experienced two processes including progress of support preparation technique and development of internal electron donor. As an impetus in development of catalyst for olefin polymerization reaction, internal electron donor has developed from monobasic acid ester such as ethyl benzoate and ethyl paraethoxybenzonate, etc. to dibasic acid esters, e.g. dibutyl phthalate, diisobutyl phthalate and dioctyl phthalate, etc., Catalysts constituted by these electron donors are ones being used extensively at present, but their activities are relatively low. In recent years, some new electron donors are reported such as succinate (CN 1313869A), maleate (EP1395617), glutarate (CN 1306544A) and aromatic acid-2,4-pentadiol ester (CN 1453298 A), etc. The activities of catalysts with these esters as electron donors are enhanced to certain degree, but the enhancement is not obviously. Catalysts prepared with compounds such as 1,3-diether (EP1395617) and especially aromatic 1,3-diether (CN1268957A and CN1141285 A) as electron donors have the currently highest catalyst activates, in which external electron donors can also be omitted, but the relatively narrow molecular weight distribution of polyolefin restricts the application of polyolefin.

SUMMARY OF THE INVENTION

The objective of this invention is to develop new electron donors and improve performances of catalysts aiming at the defects of catalysts prepared with existing electron donors, so as to make the resultant catalysts for olefin polymerization or copolymerization reaction have relatively good comprehensive performances, and at the same time, certain performances (e.g. catalyst activity and isotacticity and molecular weight distribution of poly-alfa-olefin, etc.) of catalyst can also be adjusted as required.

This invention discloses a class of novel internal electron donor aromatic 1,4-diether having the following structural formula:

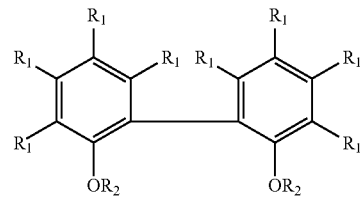
(I)

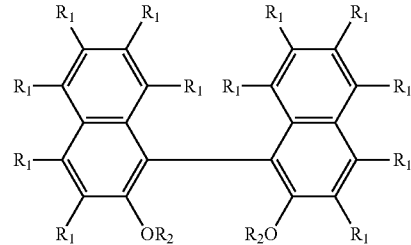
(II)

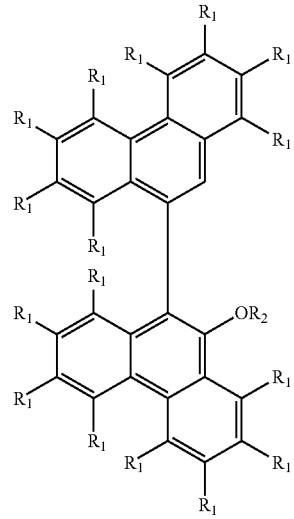
(III)

In the general formulas of (I), (II) and (III) described above:
$R_2$ is a linear or branched alkyl radical containing from 1 to 8 carbon atoms and two $R_2$ groups can be either identical or different;
$R_1$ is hydrogen, halogen, $R_3$ or $OR_3$, and two adjacent $R_3$ can bond mutually to form fused saturated or unsaturated cyclic structure; $R_3$ is selected from the group consisting of linear or branched alkyl radical containing from 1 to 20 carbon atoms, cycloalkyl radical containing from 3 to 20 carbon atoms, aryl radical containing from 6 to 20 carbon atoms and alkaryl or aralkyl radical containing from 7 to 20 carbon atoms; $R_1$ groups can be either identical or different;

The preferred aromatic 1,4-diether is 2,2'-dialkoxy-1,1'-biphenyl (I) or 2,2'-dialkoxy-1,1'-binaphthyl (II);

An environment-friendly novel technological process for preparing electron donor aromatic 1,4-diether (II) is disclosed; multiple methods are used to prepare catalysts for olefins polymerization and copolymerization; the resultant catalysts have relatively high catalytic activity and controllability, and when being used for polymerization of alfa-olefin such as propylene, the activity of catalyst can be adjusted within 40,000~150,000 gpp·g$^{-1}$ cat; the isotacticity and molecular weight distribution of polypropylene can also be adjusted in relatively wide ranges; the resultant polypropylene has favorable flowability, relatively high polymer apparent density and favorable form. The resultant catalyst system for olefin polymerization and copolymerization contain three components including: (A) solid catalyst component, (B) cocatalyst, an organoaluminum compound, and (C) the third component, an external electron donor compound. Besides elements of Ti, Mg and Cl, the solid catalyst component (A) also contains two optional combined internal electron donors: the internal electron donor combined by aromatic 1,4-diether and organic acid ester with mol ratio of 0.01~100 and the preferred mol ratio is 0.1~40; the internal electron donor combined by aromatic 1,4-diether and 1,3-diether with mol ratio of 0.01~100 and the preferred mol ratio is 0.1~30; the solid catalyst component (A) can also contain $SiO_2$ and the mol ratio of $SiO_2$ and $MgCl_2$ is 1~20;

The organic acid ester includes monobasic acid ester and dibasic acid ester, in which monobasic acid ester can be ethyl benzoate, butyl benzoate, ethyl methoxybenzoate and ethyl ethoxybenzoate, etc.; dibasic acid ester can be diethyl phthalate, dibutyl phthalate, diisobutyl phthalate and dioctyl phthalate, etc., 1,3-diether includes 9,9-bis(methoxymethyl)fluorene and 2,2-dialkyl-1,3-dimethoxy propane with large steric hindrance, such as 2,2-diisopropyl-1,3-dimethoxypropane, 2,2-dibutyl-1,3-dimethoxypropane, 2,2-diisobutyl-1,3-dimethoxypropane, 2,2-ditert-butyl-1,3-dimethoxypropane, 2,2-diisopentyl-1,3-dimethoxypropane, 2,2-ditert-pentyl-1,3-dimethoxypropane, 2,2-diphenyl-1,3-dimethoxypropane and 2,2-dibenzyl-1,3-dimethoxypropane, etc.

The titanium compound for preparing component (A) of catalyst is selected from the group consisting of compound with chemical formula of $Ti(OR')_m X_{4-m}$, wherein R' is an alkyl radical containing from 1 to 8 carbon atoms, X is chlorine and $0 \leq m \leq 4$, and $TiCl_3$. It is more convenient to use titanium tetrachloride and tetraalkoxy titanium.

The procedure for preparing the solid catalyst component (A) is as follows: form an alcoholate through reaction of anhydrous magnesium chloride and alcohol at 110~150° C., then make the alcoholate react with titanium compound and internal electron donors at 100~120° C. for 1~2 h; filter the solution and add titanium compound into the solid again to make them react at 100~120° C. for 1~2 h; repeat this procedure for 1 to 3 times; scrub the product with inactive solvent and then obtain the component (A) after vacuum drying; The reaction of alcoholate and titanium compound must be conducted at −10~−30° C. The following three methods were approved to be preferred through practice:

One of the methods is as follows: prepare a stable alcoholate through reaction of anhydrous magnesium chloride and alcohol in inactive hydrocarbon solvent at 110~140° C. for 2~5 h in presence of electron donors (or a complex formed by electron donors and titanium compound); add the alcoholate into titanium compound dropwise and make them react at 100-120° C. for 1-2 h in presence of internal electron donors; add the filtered solid into the titanium compound again and make them react at 100-120° C. for 1-2 h for another time; repeat above procedures for 1 to 3 times; scrub the product with inactive solvent and then obtain the solid catalyst component finally after vacuum drying;

The second method is as follows: prepare a stable alcoholate through reaction of anhydrous magnesium chloride and excessive alcohol at 110-140° C.; decrease the temperature and add treated $SiO_2$; raise the temperature to 110~140° C. again and make them continue to react for 1~3 h, and then obtain the support with favorable flowability after vacuum treatment. Add this support into titanium compound and make them react at 100-120° C. for 1-2 h in presence of internal electron donors. Add the filtered solid into the titanium compound again and make them react at 100-120° C. for 1-2 h for another time; repeat above procedures for 1 to 3 times; scrub the resultant product with inactive solvent and then obtain the solid catalyst component finally after vacuum drying.

The third method is as follows: make magnesium chloride react with alcohol in mineral oil at 110~150° C. and the prepared alcoholate is dispersed in the mineral oil; disperse the alcoholate scattering in the mineral oil into liquid drops by high speed dispersion emulsion or other means; spray the liquid drops into low temperature receiving solvent to make emulsion drops solidify into microballoons due to shock cooling. A method to prepare spherical alcoholate was once disclosed in China patent ZL94103454.2. After being scrubbed with inactive solvent and dried in vacuum environment, this spherical alcoholate is added into titanium compound and react for 1-2 h at 100-120° C. in presence of internal electron donors; add the filtered solid into the titanium compound again and make them react at 100-120° C. for 1-2 h for another time; repeat above procedures for 1 to 3 times; scrub the resultant product with inactive solvent and then dry it to obtain the solid catalyst component. The specific surface area of the solid catalyst component (A) prepared according to the method described above is 100~400 $m^2/g$ and its factor of porosity is 0.4-1.5 $cm^3/g$.

Cocatalyst component (B) is an organoaluminum compound with chemical formula of $R_m AlX_{3-m}$, wherein R is a linear or branched alkyl radical containing from 1 to 8 carbon atoms, X is halogen and $1 \leq m \leq 3$. Using triethyl aluminum and triisobutyl aluminum is convenient.

The third component, an external electron donor compound, can be an organic silicon, ether, ester or heterocyclic compound. The general formula of organic silicon compound is $R^1_a R^2_b Si(OR^3)_c$, where $R^1$ and $R^2$ can be identical or different; $R^1$ and $R^2$ can be alkyl, cycloalkyl or aryl radicals containing from 1 to 18 carbon atoms; $R^3$ is a linear or branched alkyl radical containing from 1 to 4 carbon atoms; a, b and c are integers, $0 \leq a \leq 3$, $0 \leq b \leq 3$, $1 \leq c \leq 3$ and $a+b+c=4$. The concrete examples of organic silicon compound include: dimethyldimethoxysilane, diethyldimethoxysilane, dipropyldimethoxysilane, dibutyldimethoxysilane, diisobutyldimethoxysilane, dicyclopentyldimethoxysilane, dicyclohexyldimethoxysilane, diphenyldimethoxysilane, methyltertbutyldimethoxysilane, methylcyclopentyldimethoxysilane, methylcyclohexyldimethoxysilane, methylphenyldimethoxysilane, methyltrimethoxysilane, ethyltrimethoxysilane, propyltrimethoxysilane, isopropyltrimethoxysilane, butyltrimethoxysilane, isobutyltrimethoxysilane, methyltriethoxysilane, ethyltriethoxysilane, propyltriethoxysilane, isopropyltriethoxysilane, butyltriethoxysilane, cyclopentyltrimethoxysilane, cyclohexytrimethoxysilane, cyclopentyltriethoxysilane, cyclohexytriethoxysilane, phenyltrimethoxysilane, phenyltriethoxysilane. The other optional external electron donor compound is aromatic 1,4-diether. If the combination of aromatic 1,4-diether and 1,3-diether is employed as the internal electron donor of catalyst used for olefins polymerization, a poly-alfa-olefin with relatively high isotacticity can also be obtained without utilization of external electron donors.

In this invention, a two-step method is adopted to prepare the internal electron donor aromatic 1,4-diether (II). In the first step, use ferric chloride solution to heterogeneously oxidize and couple 2-naphthol or its derivatives into intermediate 2,2'-dihydroxyl-1,1'-binaphthyl or its derivatives; use hydrogen peroxide to oxidize ferrous chloride into ferric chloride, which can be used to oxidize and couple 2-naphthol or its derivatives into 2,2'-dihydroxyl-1,1'-binaphthyl or its derivatives again; the hydrogen peroxide is deoxidized into water, which does not increase the complexity of the system and can continuously supply small amount of iron salt and water lost in the process, and at the time, the oxidant ferric chloride can be recycled. This method not only reserves the advantages of using ferric chloride as oxidant, but also eliminates pollutions of iron salt on environment. In the second step, add the separated intermediate 2,2′-dihydroxyl-1,1′-binaphthyl or its derivatives into alkali solution, hydrocarbon solvent, phase-transfer catalyst and etherification reagent successively to turn it into aromatic 1,4-diether (II) through reaction at 20-90 by using the phase-transfer catalysis technique of three-phase; filter out the solid and scrub it with hydrocarbon solvent, dilute alkali solution and water successively, and then dry it to obtain solid aromatic 1,4-diether (II). Separate hydrocarbon solvent from the filtrate and cleaning solution, refine the hydrocarbon solvent and recover the solid wastes. The refined hydrocarbon solvent can be recycled. These two steps of reactions constitute a environment-friendly synthesis technique.

The derivatives of 2-naphthol for synthesis of aromatic 1,4-diether (II) is

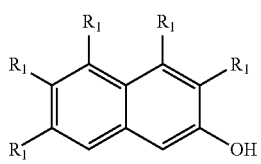

(IV)

In the general formula (IV), $R_1$ is selected from the group consisting of halogen, hydrogen, linear or branched alkyl radical containing from 1 to 16 carbon atoms, cycloalkyl radical containing from 3 to 20 carbon atoms, aryl radical containing from 6 to 20 carbon atoms and alkaryl or aralkyl radical containing from 7 to 20 carbon atoms; $R_1$ groups can be either identical or different.

Its concrete examples are 6-halogen-2-naphthol, 6-methyl-2-naphthol, 6-ethyl-2-naphthol, 6-propyl-2-naphthol, 6-butyl-2-naphthol, 6-isobutyl-2-naphthol, 6-tertbutyl-2-naphthol, 6-hexyl-2-naphthol, 6-octyl-2-naphthol, 6-dodecyl-2-naphthol, 5,6-dimethyl-2-naphthol, 5,6-diethyl-2-naphthol, 5,6-dipropyl-2-naphthol, 5,6-dibutyl-2-naphthol, 5,6-diisobutyl-2-naphthol, 5,6-ditertbutyl-2-naphthol, 5,6-dihexyl-2-naphthol, 5,6-dioctyl-2-naphthol or 5,6-docosyl-2-naphthol.

The alkali solution in the second step of reaction described above is selected from the group consisting of lithium hydroxide, sodium hydroxide, potassium hydroxide, sodium carbonate and potassium carbonate solution;

The hydrocarbon solvent can be benzene, methylbenzene, dimethylbenzene, hexane, heptane, octane, cyclohexane or their mixture; the phase-transfer catalyst is a compound with chemical formula of $R^1R^2R^3R^4N^+X^-$, wherein $R^1$, $R^2$, $R^3$ and $R^4$ can be either identical or different; R in $R^1$, $R^2$, $R^3$ and $R^4$ is selected from the group consisting of linear or branched alkyl radical containing from 1 to 16 carbon atoms, cycloalkyl radical containing from 3 to 16 carbon atoms, aryl radical containing from 6 to 16 carbon atoms and alkaryl or aralkyl radical containing from 7 to 16 carbon atoms; X is selected from the group consisting of chlorine, bromine, iodine and hydrogen sulfate radical; the etherification reagent is selected from the group consisting of dimethyl sulfate, diethyl sulfate, dimethyl carbonate, diethyl carbonate and a compound with chemical formula of RX, wherein R is a linear or branched alkyl radical containing from 1 to 12 carbon atoms and X is selected from the group consisting of chlorine, bromine, iodine and hydroxyl.

Olefins Polymerization Method

The olefins polymerization methods in this invention are known slurry polymerization, gas phase polymerization and bulk polymerization. In bulk polymerization, add olefin, cocatalyst organoaluminum compound and the third component external electron donor compound quantitatively into an autoclave firstly, and then add the prepared solid catalyst component into the autoclave according to certain mol ratio (cocatalyst organoaluminum compound/solid catalyst component) (counted as per titanium); after guiding in hydrogen, shut off the fill valve and heat the autoclave; raise the temperature to reaction temperature and maintain an isothermal reaction until the polymerization reaction finishes. After cooling the autoclave temperature to room temperature, separate and dry the polyolefin and then test their physical and chemical properties.

The polymerization reaction in this invention is usually conducted at temperature between 40~150° C. When the polymerization reaction is conducted in gas phase, the operating pressure usually ranges from 1 to 4 MPa. The operating pressure of slurry polymerization usually ranges from 0.1 to 2 Mpa. The operating pressure in bulk polymerization usually ranges from 1 to 5 MPa.

The internal electron donor 2,2′-dialkoxy-1,1′-binaphthyl and derivative thereof are prepared by adopting two-step method in the invention. In the first step, using a ferric chloride solution to heterogeneously oxidize and couple 2-naphthol or its derivatives into an intermediate designated as 2,2′-dihydroxyl-1,1′-binaphthyl or its derivatives, and filtering the solution to obtain the intermediate 2,2′-dihydroxyl-1,1′-binaphthyl or its derivatives, oxidizing ferrous chloride in the filtrate to generate ferric chloride by hydrogen peroxide, and the ferric chloride is reused for the reaction in which 2-dinaphthyl or derivative thereof is oxidative coupling to obtain 2,2′-dihydroxy-1,1′-dinaphthyl or derivative thereof, and the hydrogen peroxide, which is green oxidant, is reduced to water so as not increase the system complexity. A small amount of ferric salts and water lost in the process are ceaselessly compensated so that the oxidant, i.e. the ferric chloride, can be recycled. The method not only keeps the advantages of the ferric chloride as oxidant, but also eliminates the environmental pollution caused by ferric salts, and in addition, the method realizes closed cycle and accordingly, is a green synthetic method.

In the second step, the intermediate 2,2′-dihydroxy-1,1′-dinaphthyl or derivative thereof, separated out in the first step, is sequentially added with alkali solution, hydrocarbon solvent or alcohol solvent, phase transfer catalyst and etherification reagent using the tri-phase phase transfer catalyst technology, and reaction is performed at the temperature from 20 to 90° C. to convert the 2,2′-dihydroxy-1,1′-dinaphthyl or derivative thereof into 1,4-aromatic diether 2,2′-dialkoxy-1,1′-binaphthyl or derivative thereof which is then filtered to obtain solid, the solid is washed by solvent, diluted alkali solution and water and then dried to obtain the solid 2,2′-dialkoxy-1,1′-binaphthyl or derivative thereof; and the hydrocarbon solvent is separated from the filtrate and the washing solution for recycling.

Further, the 2-naphthol or derivative thereof is as below:

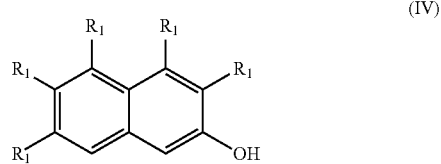

wherein $R_1$ is hydrogen, halogen, $C_1$-$C_{16}$ straight chain or branched chain alkyl, $C_3$-$C_{20}$ naphthene base, $C_6$-$C_{20}$ aryl, $C_7$-$C_{20}$ alkaryl or aralkyl; $R_1$ group may be the same or different. The special examples thereof include: 6-halogeno-2-naphthol, 6-methyl-2-naphthol, 6-ethyl-2-naphthol, 6-propyl-2-naphthol, 6-butyl-2-naphthol, 6-isobutyl-2-naphthol, 6-tert-butyl-2-naphthol, 6-hexyl-2-naphthol, 6-octyl-2-naphthol, 6-dodecyl 2-naphthol, 5,6-dimethyl-2-naphthol, 5,6-diethyl-2-naphthol, 5,6-dipropyl-2-naphthol, 5,6-dibutyl-2-naphthol, 5,6-diisobutyl-2-naphthol, 5,6-ditert-butyl-2-naphthol, 5,6-dihexyl-2-naphthol, 5,6-dioctyl-2-naphthol or 5,6-docosyl-2-naphthol, In the process of subjecting 2-dinaphthyl or derivative thereof to heterogeneous oxidative coupling by ferric chloride solution to obtain intermediate 2,2'-dihydroxy-1,1'-dinaphthyl or derivative thereof, 2-dinaphthyl or derivative thereof is suspended in the ferric chloride solution, and the molar ratio of the 2-naphthol or derivative thereof to the ferric chloride is 1:1-10. The ferric chloride solution can be formulated with $FeCl_3 \cdot 6H_2O$, and the concentration of the ferric chloride solution could have an impact on the conversion rate and the product selectivity of the 2-dinaphthyl or derivative thereof, so the concentration of the ferric chloride solution shall be moderate. The reaction temperature of oxidative coupling is 20-95° C. in general. The reaction temperature is generally 40-80° C. in consideration of energy consumption and convenient reaction control.

In the process of oxidizing ferrous chloride in the filtrate by hydrogen peroxide into ferric chloride and recycling the ferric chloride solution, the molar ratio of the amount of the hydrogen peroxide to the 2,2'-dihydroxy-1,1'-dinaphthyl or derivative thereof is relatively appropriate in the range from 0.9 to 1.2, and in general, the reaction can be completed by performing stirring reaction for 1 to 20 minutes at normal temperature. A small amount of the ferrous chloride, which could be lost in the process of recycling the ferrous chloride solution, can be compensated properly.

The alkali solution in the section step of the above reaction is lithium hydroxide solution, sodium hydroxide solution, potassium hydroxide solution, sodium carbonate solution or potassium carbonate solution.

The hydrocarbon solvent is $C_5$-$C_8$ aliphatic hydrocarbon and aromatic hydrocarbon, e.g. common pentane, hexane, heptane, octane, isooctane, cyclopentane, cyclohexane, cycloheptane, benzene, methylbenzene, ethylbenzene or their mixtures.

The alcohol solvent is $C_1$-$C_6$ aliphatic alcohol, e.g. methanol, ethanol, propanol, isopropanol, butanol, isobutanol, pentanol, isopentanol and hexanol.

The phase transfer catalyst is the compound having the chemical formula of $R^1R^2R^3R^4N^+X^-$, wherein $R^1$, $R^2$, $R^3$ and $R^4$ may be the same or different, R of $R^1$, $R^2$, $R^3$ and $R^4$ is $C_1$-$C_{16}$ straight chain or branched chain alkyl, $C_3$-$C_{16}$ naphthene base, $C_6$-$C_{16}$ aryl, $C_7$-$C_{16}$ aralkyl or alkaryl, and X is chlorine, bromine, iodine or bisulfate ion.

The etherification reagent is dimethyl sulfate, diethyl sulfate or the compound having the chemical formula of RX, wherein R is $C_1$-$C_8$ straight chain or branched chain alkyl; and X is chlorine, bromine and iodine.

In the reaction, the molar ratios of the 2,2'-dialkoxy-1,1'-binaphthyl or derivative thereof to the alkali solution, the etherification reagent and the phase transfer catalyst respectively are 1:2-3, 1:2-3 and 1:0.001-0.9. The amount of organic solvent and water shall be moderate owing to their impact on the reaction rate and the reaction time.

Description is made to the content of the invention with reference to the embodiments described below; however, the scope of the invention is not limited by the embodiments described below.

EMBODIMENTS OF THE INVENTION

Example 1 a) Preparation of Alcoholate

After the 3-opening bottle with agitator and thermometer is sufficiently swept by nitrogen gas, add 5 g anhydrous magnesium chloride, 30 ml decane and 23 ml 2-ethylhexanol in it. Agitate the reactants while raising the temperature to 130° C., and make them react at this temperature for 2 h. Add 1.5 ml tetrabutyl titanate and 2 ml diisobutyl phthalate into 5 ml methylbenzene in advance, and agitate them at room temperature for 0.5 h to obtain complex solution through the reaction. Add this methylbenzene solution into the 3-opening bottle and maintain the reaction at 130 for 1 h. After the reaction finishes, cool the reactants to room temperature to form a stable alcoholate solution.

b) Preparation of Solid Catalyst Component (A)

Sweep a reactor with agitator and thermometer sufficiently by nitrogen gas and add 200 ml titanium tetrachloride into it in advance. Keep it at −20° C. Add the prepared alcoholate solution into the reactor dropwise within 30 min. After all alcoholate solution is added, raise the temperature to 70° C.; add 3.5 mmol 2,2'-dimethoxy-1,1'-binaphthyl and continue to raise the temperature to 110; add 1.2 ml diisobutyl phthalate and maintain the reaction at this temperature for 2 h. After the reaction finishes, filter out the solution and add 200 ml titanium tetrachloride again and maintain the reaction at 110° C. for 1.5 h. After the reaction finishes, filter out the reaction liquid and scrub it with chloroform at 60° C. for 60 min firstly and then with hexane until there are no free chloride ions in the filtrate. Dry the solid product in vacuum environment to obtain the solid catalyst component (A).
Analysis results of solid catalyst component (A):
Content of titanium: 2.36% (wt); specific surface area: 246.85 m²/g; mean grin size: 22.39 μm.

c) Polymerization Reaction

An agitator with rotary speed up to 600 rpm is installed on a 2 L stainless steel autoclave. After the autoclave is sufficiently swept by nitrogen gas, add 1.5 L refined propylene and 4.0 ml hexane solution with triethyl aluminium concentration of 1 mol/L and 0.1 ml CHMMS (cyclohexylmethyldimethoxysilane) in it, and then add 0.00493 mmol solid catalyst component (A) (counted as per Ti) prepared as per step (b). Then raise the temperature to 70° C. and add hydrogen gas with fractional pressure of 0.2 MPa. Maintain the polymerization reaction at this temperature for 1.5 h. After the reaction finishes, guide in cooling water to cool the autoclave to room temperature, stop agitation and discharge unreacted gas to get the reaction product. After vacuum drying, 582 g white polymer is obtained.

Catalyst activity: 58,200 gPP/gcat; apparent density of polymer: 0.45 g/cm$^3$; d50µ710 (mean grain size of polymer is 710µ); isotactic index of polymer: 97.8% (boiling heptane extraction method).

Examples 2-3

In implementations example 2, the dosage of CHMMS in C) polymerization reaction of example 1 is changed from 0.1 ml to 0.2 ml; in implementations example 3, the reactant CHMMS in C) polymerization reaction of example 1 is replaced by 0.1 mmol 2,2′-dimethoxy-1,1′-binaphthyl; other conditions are identical with those of example 1. Their results are listed in Table 1.

TABLE 1

| Example | Content of Titanium/ (wt) % | Catalyst activity/ gPP/gCat | Polymer apparent density/g · cm$^{-3}$ | Isotactic index of polymer/% |
|---|---|---|---|---|
| 2 | 2.36 | 54,500 | 0.45 | 99.2 |
| 3 | 2.36 | 41,000 | 0.43 | 96.1 |

Examples 4-5

Replace diisobutyl phthalate in b) preparation of example 1 with 9,9-bis(methoxymethyl) fluorene and other conditions are identical with those of Example 1. The results are shown in Table 2.

TABLE 2

| Example | 9,9-bis (methoxymethyl) fluorene | Content of Titanium/ (wt) % | Catalyst activity/ gPP/gCat | Polymer apparent density/ g · cm$^{-3}$ | Isotactic index of polymer/% |
|---|---|---|---|---|---|
| 4 | 1 mmol | 2.34 | 62,000 | 0.45 | 98.2 |
| 5 | 2 mmol | 2.53 | 68,000 | 0.44 | 98.9 |

The molecular weight distribution in example 4 is as follows: Mn 80548, Mw 290065, Mp 161160, Mz 961687 and Mv 246118; the molecular weight distribution index (MWD) is 3.601.

Example 6

Synthesis of Solid Catalyst Component (A)

Successively add 4.8 g MgCl$_2$ and 48 mL n-butyl alcohol into a 3-opening bottle which is sufficiently swept by high-purity nitrogen gas. Begin to raise temperature when agitation is started, and maintain agitation for 1 h at 120° C. until MgCl$_2$ and n-butyl alcohol form a transparent solution; add 2.1 g 2,2′-dimethoxy-1,1′-binaphthyl and maintain the reaction for 1 h at this temperature before starting cooling; when the temperature is reduced to 60° C., add 9.5 g SiO$_2$, and then raise the temperature to 120° C. and react for 1 h; at last, extract out alcohol in vacuum environment to obtain white catalyst support whose mol ratio of alcohol and magnesium is 2.46 and magnesium content is 4.97%.

Add 5 g catalyst support prepared as per the said method into a glass reactor with 100 mL TiCl$_4$ in it at −20° C. and maintain this temperature for 0.5 h; start to raise temperature gradually to 60° C. in 2.5 h; add 0.75 mL ethyl benzoate (EB) into the reactor and raise the temperature gradually to 120° C.; maintain the reaction for 2 h; filter the solution, add 100 mL TiCl$_4$ again, and raise the temperature to 110° C. and react for 1.5 h; filter out the liquid and scrub the filtrate with hexane until there are no free chorine ions in it. Dry the remained solid product in vacuum environment to obtain the solid catalyst component (A), in which the content of Ti is 3.69%.

Conduct a propylene polymerization reaction according to the method in example 1, in which the catalyst activity is 53,000 gPP/gCat, the apparent density of polymer is 0.45 g·cm$^{-3}$ and the isotactic index of polymer is 98.3%.

Example 7

In accordance with the method disclosed in China patent ZL94103454.2, make magnesium chloride and alcohol react in mineral oil at 110-150° C. and the generated alcoholate scatters in the mineral oil; then disperse the alcoholate scattering in the mineral oil by Φ1.5 mm capillaries into liquid drops; spray the emulsion into low temperature receiving solvent to make emulsion drops solidify into microballoons due to shock cooling; scrub the microballoon alcoholate with inactive solvent and then obtain spherical support after vacuum drying. Sweep a reactor with agitator and thermometer sufficiently by nitrogen gas and add 200 ml titanium tetrachloride into it in advance. Keep it at −20° C., and then add 5 g prepared spherical support into the reactor. Then raise the temperature to 70° C. and add 3.0 mmol 2,2′-dimethoxy-1,1′-binaphthyl; continue to raise the temperature to 110° C. and add 1.0 ml diisobutyl phthalate; maintain the reaction for 2 h at this temperature; after filtering out liquid, add 200 ml titanium tetrachloride again and react for 1.5 h at 110° C. After the reaction finishes, filter out the reaction liquid and scrub it with methenyl chloride at 60° C. for 60 min firstly and then with hexane until there are no free chloride ions in the filtrate. Dry the solid product in vacuum environment to obtain the solid catalyst component (A). Its content of Ti is 3.12%.

Conduct a propylene polymerization reaction according to the method in example 1, in which the catalyst activity is 55,000 gPP/gCat, the apparent density of polymer is 0.45 g·cm$^{-3}$ and the isotactic index of polymer is 98.1%. The molecular weight of polymer is as follows: Mn 69915, Mw 371451, Mp 170529, Mz 1827217 and Mv 296669; the molecular weight distribution index is 5.313.

Examples 8-13

Replace diisobutyl phthalate in example 7 with 9,9-bis (methoxymethyl) fluorene and change the dosages of 2,2′-dimethoxy-1,1′-binaphthyl and 9,9-bis(methoxymethyl) fluorene; no external electron donors are added in polymerization; keep other steps unchanged. The results are shown in Table 3.

TABLE 3

| Example | 9,9-bis (methoxymethyl) fluorine g/ g support | 2,2'-dimethoxy-1,1'-binaphthyl g/ g support | Content of Ti/ (wt)% | Catalyst activity/ gPP/gCat | Polymer apparent density/ g·cm$^{-3}$ | Isotactic index of polymer/ % |
|---|---|---|---|---|---|---|
| 8  | 0.20 | 0.08 | 3.24 | 100,000 | 0.43 | 96.96 |
| 9  | 0.20 | 0.10 | 3.04 | 96,000  | 0.42 | 96.22 |
| 10 | 0.12 | 0.20 | 3.66 | 80,000  | 0.40 | 92.07 |
| 11 | 0.10 | 0.20 | 3.60 | 90,000  | 0.42 | 90.19 |
| 12 | 0.08 | 0.20 | 3.92 | 87,000  | 0.40 | 88.41 |
| 13 | 0.06 | 0.20 | 3.72 | 89,600  | 0.41 | 80.94 |

Examples 14-15

In these examples, add external electron donor diphenyldimethoxysilane (DDS) instead of adding no external electron donors in example 9 and keep other steps unchanged. The results are shown in Table 4.

TABLE 4

| Example | 9,9-bis (methoxymethyl) fluorine g/ g supportr | 2,2'-dimethoxy-1,1'-binaphthyl g/ g support | Content of Ti/ %(wt) | DDS/ ml | Catalyst activity/ gPP/gCat | Polymer apparent density/ g·cm$^{-3}$ | Isotactic index of polymer/ % |
|---|---|---|---|---|---|---|---|
| 14 | 0.20 | 0.10 | 3.04 | 01  | 51,000 | 0.40 | 97.10 |
| 15 | 0.20 | 0.10 | 3.04 | 0.2 | 43,000 | 0.40 | 98.20 |

Examples 16-17

In these two examples, replace 2,2'-dimethoxy-1,1'-binaphthyl by 2,2'-diethoxy-1,1'-binaphthyl and 2,2'-dipropoxy-1,1'-binaphthyl respectively and keep other steps unchanged. The results are shown in Table 5.

TABLE 5

| Example | aromatic 1,4-diether | Content of Ti/ (wt) % | Catalyst activity/ gPP/gCat | Polymer apparent density/g·cm$^{-3}$ | Isotactic index of polymer/% |
|---|---|---|---|---|---|
| 16 | 2,2'-diethoxy-1,1'-binaphthyl | 2.58 | 47,300 | 0.44 | 96.78 |
| 17 | 2,2'-dipropoxy-1,1'-binaphthyl | 2.42 | 41,700 | 0.44 | 96.36 |

Example 18

In this example, replace 2,2'-dimethoxy-1,1'-binaphthyl by 5,5'-ditert-butyl-2,2'-dimethoxy-1,1'-biphenyl and keep other steps unchanged. The resultant catalyst activity is 56,000 gPP/gCat, the apparent density of polymer is 0.45 g/ml and the isotactic index of polypropylene is 98.5%.

Example 19 a) Preparation of 2,2'-dihydroxy-1,1'-binaphthyl 2 g 2-naphthol, 11.4 g $FeCl_3 \cdot 6H_2O$ and 100 ml water are added to a 200 ml flask in order to perform stirring reaction in 65° C. water bath, TLC (thin layer chromatography) is adopted for tracking, the reaction product is filtered 3 hours after the reaction to obtain the solid 2,2'-dihydroxy-1,1'-binaphthyl, the 2,2'-dihydroxy-1,1'-binaphthyl is washed with 50 ml water, the washing solution is incorporated into the filtrate, 7.5 ml $H_2O_2$ with the concentration of 30% is slowly and dropwise added to the filtrate under stirring, the filtrate is continuously stirred for 10 minutes, 2 g 2-naphthol is added to perform stirring reaction at 65° C., TLC tracking is performed until the reaction comes to an end, and the reaction product is filtered to obtain the solid 2,2'-dihydroxy-1,1'-binaphthyl.

The above steps are repeated so as to lead to the results in Table 6. The HPLC analysis result of the eleventh circular reaction product shows that the conversion rate of the 2-naphthol is more than 98%, and the selectivity of the 2,2'-dihydroxy-1,1'-binaphthyl is more than 99%.

TABLE 6

| Cycle Times | Reaction Time/h | TLC Product Analysis |
|---|---|---|
| 0  | 3   | Disappearance of Raw Material Spot |
| 1  | 3   | Disappearance of Raw Material Spot |
| 2  | 3   | Disappearance of Raw Material Spot |
| 3  | 3.5 | Disappearance of Raw Material Spot |
| 4  | 3.5 | Disappearance of Raw Material Spot |
| 5  | 3.5 | Disappearance of Raw Material Spot |
| 6  | 3.5 | Disappearance of Raw Material Spot |
| 7  | 4   | Disappearance of Raw Material Spot |
| 8  | 4   | Disappearance of Raw Material Spot |
| 9  | 4   | Disappearance of Raw Material Spot |
| 10 | 4   | Disappearance of Raw Material Spot |
| 11 | 4   | A Small Amount of Raw Material | b) Preparation of 2,2'-dimethoxy-1,1'-binaphthyl 52 g NaOH with the concentration of 30% is formulated at room temperature. Under stirring, 143 g 2,2'-dihydroxy-1,1'- binaphthyl prepared according to the above method, 5.2 g tetrabutylammonium hydrogen sulfate and 500 ml methylbenzene are heated up to 70° C. while being dropwise added with 164 g dimethyl sulfate in order to perform stirring reaction, which is followed by TLC tracing, and upon the disappearance of monoether spots, the reaction continues for a while. The reaction product is cooled and filtered, the filter cake is washed sequentially with 400 ml methylbenzene and 400 ml NaOH solution with the concentration of 5%, then washed with water to be neutral and finally dried to obtain the 2,2'-dimethoxy-1,1'-binaphthyl. The HPLC analysis result shows that the conversion rate of the 2,2'-dihydroxy-1,1'-binaphthyl is more than 99%, the purity of the 2,2'-dimethoxy-1,1'-binaphthyl is more than 98% and the yield of the 2,2'-dimethoxy-1,1'-binaphthyl is more than 95%. Methylbenzene layers are merged to separate out the methylbenzene for recycling.

Example 20

6-Tert-butyl-2-naphthol is used for replacing the 2-naphthol in Example 19, other raw materials, proportions of the raw materials and operation steps are unchanged, and 2.6 g 6,6'-ditert-butyl-2,2'-dimethoxy-1,1'-binaphthyl crystal is obtained.

Example 21

2.0 g 2,2'-Dihydroxy-1,1'-binaphthyl prepared in the step a) of the Embodiment 1, 0.65 g NaOH, a small amount of water, 20 mL methylbenzene and 0.2 g tetrabutylammonium bromide are sequentially added to a round bottom flask in order to perform stirring reaction at normal temperature, 4.0 ml $(CH_3CH_2O)_2SO_2$ is dropwise added to the round bottom flask within 20 minutes, and after the reaction is performed for 6 hours while heating and then preserving the temperature of the water bath at 50° C., the reaction product is cooled and filtered, the filter cake is washed respectively with alkali solution and water and then drained to obtain 2.4 g 2,2'-diethoxy-1,1'-binaphthyl crystal.

Example 22

14.3 g 2,2'-Dihydroxy-1,1'-binaphthyl prepared in the step a) of the Example 19, 5.2 g sodium hydroxide, 16.4 g $(CH_3O)_2SO_2$, 0.5 g tetrabutylammonium hydrogen sulfate, 40 ml methylbenzene and 40 ml water are sequentially added to a round bottom flask to perform stirring reaction at 70° C., and after the reaction is performed for 4 hours, the yield of 2,2'-dimethoxy-1,1'-binaphthyl is more than 85.5% and the purity of the 2,2'-dimethoxy-1,1'-binaphthyl is more than 97.5%.

Example 23

14.3 g 2,2'-Dihydroxy-1,1'-binaphthyl prepared in the step a) of the Example 19, 40 ml sodium hydroxide with the concentration of 7.5%, 0.5 g tetrabutylammonium hydrogen sulfate and 40 ml methylbenzene are added to a round bottom flask with the volume of 100 mL. 16.4 g dimethyl sulfate is dropwise added to the round bottom flask to perform stirring reaction at 70° C.; and after the reaction is performed for 4 hours, the reaction product is filtered to obtain 2,2'-dimethoxy-1,1'-binaphthyl. The methylbenzene is separated from the filtrate. The aforementioned reaction is repeated, and recycling of the methylbenzene five times leads to the results in Table 7.

TABLE 7

| | Recycling Times of Methylbenzene | | | | | |
|---|---|---|---|---|---|---|
| | 0 | 1 | 2 | 3 | 4 | 5 |
| Yield/% of 2,2'-dimethoxy-1,1'-binaphthyl | 85.5 | 94.0 | 95.7 | 96.0 | 94.7 | 95.4 |

Example 24

20 ml Water, 0.65 g NaOH and 2.0 g 2,2'-dihydroxy-1,1'-binaphthyl prepared in the step a) of the Example 19 are added to a round bottom flask with the volume of 100 mL, 4.0 ml $(CH_3CH_2O_2)SO_2$ is dropwise added to the round bottom flask under stirring, 0.2 g tetrabutylammonium bromide and 10 ml ethanol are added 20 minutes after the dropwise addition in order to begin heating, the temperature of the water bath is constantly maintained at 50° C., no raw material is detected by means of TLC after the reaction is performed for 6 hours, and the reaction is put to stoppage. The reaction product is poured, while hot, into 50 g crushed ice, followed by filtration to further obtain 2,2'-diethoxy-1,1'-binaphthyl with the yield of 95.6%, the melting point of 92° C. and the content, according to HLPC detection, of 97.2%.

Example 25

1.0 g NaOH, 20 ml water and 2.8 g 2,2'-dihydroxy-1,1'-binaphthyl prepared in the step a) of the Example 19 are added to a round bottom flask with the volume of 100 mL, 3.7 g bromopropane, 0.2 g tetrabutylammonium bromide and 10 ml ethanol are dropwise added to the round bottom flask, the temperature of the water bath is 70° C., and after the reaction is performed for 4 hours, the reaction product is poured, while hot, into 50 g crushed ice, followed by separating crystal out. The crystal is filtered and the filter cake is washed with diluted alkali solution and icy water as well as recrystallized with ethanol to obtain white crystal 2,2'-dipropoxy-1,1'-binaphthyl with the yield of 93.7%, the melting point of 87° C. and the content, according to HLPC detection, of 96.4%.

Example 26

1.0 g NaOH, 20 ml water and 2.8 g 2,2'-dihydroxy-1,1'-binaphthyl prepared in the step a) of the Example 19 are added to a round bottom flask with the volume of 100 mL and are then stirred to be dissolved, 4.1 g n-butyl bromide, 0.2 g tetrabutylammonium bromide and 10 ml ethanol are dropwise added to the round bottom flask, the temperature of the water bath is maintained at 70° C., and after the reaction is performed for 4 hours, the reaction product is poured, while hot, into 50 g crushed ice, followed by stirring to further separate crystal out. The crystal is filtered the filter cake is washed with alkali solution and icy water to obtain light yellow granular solid. The solid is recrystallized with ethanol to obtain yellow-white crystal 2,2'-dibutoxy-1,1'-binaphthyl with the yield of 92.3%, the melting point of 85° C. and the content, according to HLPC detection, of 96.6%.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

We claim:
1. A preparation method of 2,2'-dialkoxy-1,1'-binaphthyl compound, comprising the following two-step reaction:
   a) at the reaction temperature from 20 to 95° C., using a ferric chloride solution to heterogeneously oxidize and couple a 2-naphthol compound into an intermediate designated as 2,2'-dihydroxyl-1,1'-binaphthyl compound, and filtering the solution to obtain the intermediate 2,2'-dihydroxyl-1,1'-binaphthyl compound, oxidizing ferrous chloride in the filtrate to generate ferric chloride by hydrogen peroxide, and reusing ferric chloride in the filtrate solution; and
   b) causing the intermediate 2,2'-dihydroxyl-1,1'-binaphthyl compound to turn into a 2,2'-dialkoxy-1,1'-binaphthyl compound of formula II formula II

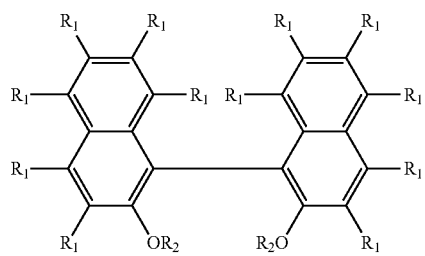

by a tri-phase phase-transfer process in presence of an alkali solution, an organic solvent, a phase-transfer catalyst and an etherification reagent at 20-90° C., filtering the 2,2'-dialkoxy-1,1'-binaphthyl compound of formula II, washing the 2,2'-dialkoxy-1,1'-binaphthyl compound of formula II successively with an organic solvent, 5% sodium hydroxide solution and water, and drying the 2,2'-dialkoxy-1,1'-binaphthyl compound of formula II to obtain the 2,2'-dialkoxy-1,1'-binaphthyl compound, separating the organic solvent from the filtrate and the washout solution, and reusing the organic, wherein:
   $R_2$ is a linear or branched alkyl radical containing from 1 to 8 carbon atoms, and the two $R_2$ groups in formula II is either identical or different;
   $R_1$ is hydrogen, halogen, $R_3$ or $OR_3$, and two adjacent $R_3$ groups are capable of bonding mutually to form fused saturated or unsaturated cyclic structure; $R_3$ is selected from the group consisting of linear or branched alkyl radical containing from 1 to 20 carbon atoms, cycloalkyl radical containing from 3 to 20 carbon atoms, aryl radical containing from 6 to 20 carbon atoms and alkaryl or aralkyl radical containing from 7 to 20 carbon atoms; $R_1$ groups are either identical or different.
2. The method of claim 1, wherein the 2-naphthol compound is

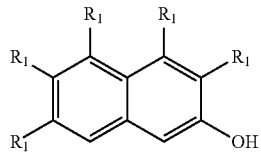

wherein $R_1$ groups are identical or different and are independently selected from the group consisting of halogen, hydrogen, linear or branched alkyl radical containing from 1 to 16 carbon atoms, cycloalkyl radical containing from 3 to 20 carbon atoms, aryl radical containing from 6 to 20 carbon atoms, and alkaryl or aralkyl radical containing from 7 to 20 carbon atoms.
3. The method of claim 1, wherein the step (a), the 2-naphthol is suspended in the ferric chloride solution, and the molar ratio of the 2-naphthol to the ferric chloride is 1:1-10.
4. The method of claim 1, wherein the step (a), the molar ratio of the hydrogen peroxide to the 2-naphthol is 0.9-1.2, stirring reaction is performed for 1 to 20 minutes at normal temperature; and the ferric chloride lost in the process of recycling the ferric chloride solution is compensated.
5. The method of claim 1, wherein the step (b), the organic solvent is a hydrocarbon solvent or alcohol solvent, the hydrocarbon solvent is selected from aliphatic hydrocarbon or aromatic hydrocarbon containing from 5 to 8 carbon atoms; and the alcohol solvent is selected from alcohol containing from 1 to 6 carbon atoms;
   wherein the phase-transfer catalyst is a compound with a chemical formula of $R^1R^2R^3R^4N^+X^-$, where $R^1$, $R^2$, $R^3$ and $R^4$ are identical or different and are independently selected from linear or branched alkyl radical containing from 1 to 16 carbon atoms, cycloalkyl radical containing from 3 to 16 carbon atoms, aryl radical containing from 6 to 20 carbon atoms, or alkaryl or aralkyl radical containing from 7 to 20 carbon atoms, and X is selected from chlorine, bromine, iodine or hydrogen sulfate radical;
   wherein the etherification reagent is selected from dimethyl sulfate, diethyl sulfate, dimethyl carbonate, diethyl carbonate, or a compound with chemical formula of RX where R is a linear or branched alkyl radical containing from 1 to 8 carbon atoms and X is chlorine, bromine or iodine; and
   wherein:
   the alkali solution is selected from lithium hydroxide, sodium hydroxide, potassium hydroxide, sodium carbonate, or potassium carbonate solutions; and
   the molar ratios of the 2,2'-dialkoxy-1,1'-binaphthyl compound to the alkali solution, the etherification reagent and the phase transfer catalyst respectively are 1:2-3, 1:2-3 and 1:0.001-0.9.

* * * * *